US009156785B2

(12) United States Patent
Aqad et al.

(10) Patent No.: US 9,156,785 B2
(45) Date of Patent: Oct. 13, 2015

(54) BASE REACTIVE PHOTOACID GENERATORS AND PHOTORESISTS COMPRISING SAME

(75) Inventors: Emad Aqad, Northborough, MA (US); Mingqi Li, Shrewsbury, MA (US); Cheng-Bai Xu, Southboro, MA (US); Deyan Wang, Hudson, MA (US); Cong Liu, Shrewsbury, MA (US); Joon Seok Oh, Natick, MA (US); Shintaro Yamada, Shrewsbury, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 71 days.

(21) Appl. No.: 13/296,949

(22) Filed: Nov. 15, 2011

(65) Prior Publication Data
US 2012/0129108 A1 May 24, 2012

Related U.S. Application Data

(60) Provisional application No. 61/458,014, filed on Nov. 15, 2010.

(51) Int. Cl.
*G03F 7/004* (2006.01)
*G03F 7/30* (2006.01)
*C07C 303/32* (2006.01)
*C07C 309/19* (2006.01)
*C07C 309/24* (2006.01)
*C08F 220/22* (2006.01)
*C08F 228/02* (2006.01)
*C07C 309/04* (2006.01)
*C07C 309/08* (2006.01)
*C07C 309/06* (2006.01)
*C07C 309/12* (2006.01)
*C07C 309/20* (2006.01)
*C07C 309/23* (2006.01)
*C07C 381/12* (2006.01)
*G03F 7/38* (2006.01)
*C07C 63/72* (2006.01)
*C07C 309/17* (2006.01)
*G03F 7/038* (2006.01)
*G03F 7/039* (2006.01)
*G03F 7/20* (2006.01)

(52) U.S. Cl.
CPC .............. *C07C 381/12* (2013.01); *C07C 63/72* (2013.01); *C07C 303/32* (2013.01); *C07C 309/04* (2013.01); *C07C 309/06* (2013.01); *C07C 309/08* (2013.01); *C07C 309/12* (2013.01); *C07C 309/17* (2013.01); *C07C 309/19* (2013.01); *C07C 309/20* (2013.01); *C07C 309/23* (2013.01); *C07C 309/24* (2013.01); *C08F 220/22* (2013.01); *C08F 228/02* (2013.01); *G03F 7/0045* (2013.01); *G03F 7/0046* (2013.01); *G03F 7/0382* (2013.01); *G03F 7/0397* (2013.01); *G03F 7/38* (2013.01); *C07C 2102/42* (2013.01); *G03F 7/2041* (2013.01)

(58) Field of Classification Search
CPC .. C07C 303/32; C07C 309/19; C07C 309/24; C07C 2102/42; C07C 381/12; C07C 309/04; C07C 309/06; C07C 309/08; C07C 309/12; C07C 309/17; C07C 309/20; C07C 309/23; G03F 7/0045; G03F 7/0397; G03F 7/0046; G03F 7/2041; G03F 7/38; C08F 220/22; C08F 228/02
USPC ......... 430/270.1, 326, 921, 922, 330; 562/41, 562/42, 100, 109, 113; 526/243, 256; 560/14, 126, 151, 229
See application file for complete search history.

(56) References Cited

U.S. PATENT DOCUMENTS

| | | | |
|---|---|---|---|
| 5,128,232 A | 7/1992 | Thackeray et al. | |
| 5,492,793 A | 2/1996 | Breyta et al. | |
| 5,879,856 A * | 3/1999 | Thackeray et al. | 430/270.1 |
| 6,042,997 A | 3/2000 | Barclay et al. | |
| 6,239,131 B1 | 5/2001 | Shinozaki et al. | |
| 6,280,898 B1 | 8/2001 | Hasegawa et al. | |
| 6,492,091 B2 | 12/2002 | Kodama et al. | |
| 6,841,333 B2 | 1/2005 | Lamanna et al. | |
| 7,041,838 B2 | 5/2006 | Kamon et al. | |
| 7,122,294 B2 | 10/2006 | Lamanna | |
| 7,122,589 B2 | 10/2006 | Nishiyama et al. | |
| 7,432,035 B2 | 10/2008 | Maeda et al. | |
| 7,439,006 B2 | 10/2008 | Yoshida et al. | |
| 7,514,202 B2 * | 4/2009 | Ohsawa et al. | 430/270.1 |
| 7,524,609 B2 * | 4/2009 | Wada | 430/270.1 |
| 7,531,290 B2 * | 5/2009 | Kobayashi et al. | 430/270.1 |
| 7,569,326 B2 * | 8/2009 | Ohsawa et al. | 430/270.1 |
| 7,611,822 B2 * | 11/2009 | Takemoto | 430/270.1 |
| 7,612,217 B2 * | 11/2009 | Sakamoto et al. | 549/13 |
| 7,700,256 B2 | 4/2010 | Barclay et al. | |
| 7,968,268 B2 | 6/2011 | Wang | |
| 8,057,985 B2 * | 11/2011 | Ohashi et al. | 430/270.1 |
| 8,435,717 B2 | 5/2013 | Hagiwara et al. | |
| 2008/0227032 A1 * | 9/2008 | Ober et al. | 430/281.1 |

(Continued)

FOREIGN PATENT DOCUMENTS

EP 0 164 248 B1 10/1991
EP 0 232 972 B1 9/1993

(Continued)

Primary Examiner — John S Chu
(74) Attorney, Agent, or Firm — S. Matthew Cairns

(57) ABSTRACT

This invention relates to new photoacid generator compounds and photoresist compositions that comprise such compounds. In particular, the invention relates to photoacid generator compounds that comprise base-cleavable groups.

10 Claims, No Drawings

(56) References Cited

U.S. PATENT DOCUMENTS

| | | |
|---|---|---|
| 2009/0117489 A1 | 5/2009 | Wang et al. |
| 2009/0234155 A1* | 9/2009 | Oh et al. ................. 562/100 |
| 2009/0269696 A1* | 10/2009 | Ohsawa et al. ............ 430/270.1 |
| 2010/0035185 A1* | 2/2010 | Hagiwara et al. .......... 430/286.1 |
| 2010/0081088 A1 | 4/2010 | Kawaue et al. |
| 2010/0099042 A1 | 4/2010 | Ohashi et al. |
| 2010/0183975 A1* | 7/2010 | Takahashi et al. ......... 430/270.1 |
| 2010/0304292 A1 | 12/2010 | Ichikawa et al. |
| 2011/0003257 A1 | 1/2011 | Wang et al. |
| 2011/0159429 A1 | 6/2011 | Thackeray et al. |

FOREIGN PATENT DOCUMENTS

| | | |
|---|---|---|
| EP | 0 783 136 A2 | 7/1997 |
| EP | 0 829 766 A2 | 3/1998 |
| EP | 1780198 A1 | 10/2006 |
| EP | 2105794 A1 | 3/2009 |

* cited by examiner

BASE REACTIVE PHOTOACID GENERATORS AND PHOTORESISTS COMPRISING SAME

This application claims the benefit of priority under 35 U.S.C. §119(3) to U.S. Provisional Application No. 61/458,014, filed on Nov. 15, 2010, the entire contents of which are incorporated by reference.

This invention relates to new photoacid generator compounds ("PAGs") and photoresist compositions that comprise such compounds. In particular, the invention relates to photoacid generator compounds that comprise base-reactive groups. Positive- and negative-acting chemically amplified resists that contain such PAGs and that are imaged with short wavelength radiation such as sub-300 nm and sub-200 nm radiation are particularly preferred.

Photoresists are photosensitive films for transfer of images to a substrate. They form negative or positive images. After coating a photoresist on a substrate, the coating is exposed through a patterned photomask to a source of activating energy such as ultraviolet light to form a latent image in the photoresist coating. The photomask has areas opaque and transparent to activating radiation that define an image desired to be transferred to the underlying substrate. A relief image is provided by development of the latent image pattern in the resist coating. The use of photoresists is generally well-known to those skilled in the art.

Known photoresists can provide features having resolution and size sufficient for many existing commercial applications. However for many other applications, the need exists for new photoresists that can provide highly resolved images of sub-micron dimension.

Various attempts have been made to alter the make-up of photoresist compositions to improve performance of functional properties. For example, attempts have been made to improve photoresist performance by altering the PAGs used. For example, see U.S. 2010/0081088 which discloses, among other things, a variety of photoactive compounds for use in photoresist compositions. Certain of the PAGs disclosed in U.S. 2010/0081088 having an ester moiety on the PAG sulfonium cation posses extremely slow base promoted dissociation, and thereby provide no to minimal benefit to the lithographic performance of the photoresist.

There remains a need for photoacid generators having relatively fast base promoted dissolution rates. Such photoacid generators may assist in lithographic performance of photoresists, such as exhibiting reduced defects associated with a resist relief image formed from the photoresist composition, and/or providing improved exposure latitude (EL), and/or reduced mask error factor (MEF).

We have now discovered novel photoacid generator compounds (PAGs) for use in either positive-acting or negative-acting photoresist compositions. In particular, photoacid generator compounds are provided that have one or more base-reactive moieties, particularly base-reactive moieties that are reactive after exposure and post-exposure lithographic processing steps. Preferably, the base-reactive moiety will react upon treatment with aqueous alkaline developer compositions, such as 0.26N tetramethylammonium hydroxide aqueous developer compositions.

The present invention provides a photoacid generator compound of formula (I) or (II)

(I)

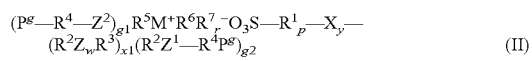

(II)

wherein each $R^1$ is chosen from $(C_1$-$C_{10})$alkyl, heteroatom-containing $(C_1$-$C_{10})$alkyl, fluoro$(C_1$-$C_{10})$alkyl, heteroatom-containing fluoro$(C_1$-$C_{10})$alkyl, $(C_6$-$C_{10})$aryl, and fluoro$(C_6$-$C_{10})$aryl; each $R^2$ is a chemical bond or a $(C_1$-$C_{30})$ hydrocarbyl group; each $R^3$ is H or a $(C_1$-$C_{30})$hydrocarbyl group; each $R^4$ is a chemical bond or a $(C_1$-$C_{30})$hydrocarbyl group; $R^5$, $R^6$ and $R^7$ independently are chosen from an optionally substituted carbocyclic aryl group, an allyl group, and an optionally substituted $(C_1$-$C_{20})$alkyl group; X is a chemical bond or a divalent linking group; Z is chosen from a β-heteroatom-substituted lactone, an acetoacetoxy ester, —C(O)—O—C(O)—$R^1$—, —C(CF$_3$)$_2$O—, —COO—$R^f$—, —SO$_3$—$R^f$—, —OCH$_{3-z}$(CH$_2$OC(=O)—$R^f$—)$_z$, and a $(C_5$-$C_{30})$cyclohydrocarbyl group comprising a base-reactive group; $Z^1$ is a divalent base-reactive group; $Z^2$ is chosen from a β-heteroatom-substituted lactone, —C(O)—O—C(O)—$R^1$—, an acetoacetoxy ester, —COO—$R^f$—, —SO$_3$—$R^f$—, —CH$_{3-z}$(CH$_2$OC(=O)—$R^f$—)$_z$, and a $(C_5$-$C_{30})$cyclohydrocarbyl group comprising a base-reactive group; each $R^f$ is independently a fluoro$(C_1$-$C_{10})$alkyl; $P^g$ is a polymerizable group; p=0-6; w=1-3; x=1-4; x1=0-4; y=0-5; z=1-2; g1=0-3; g2=0-3; r=0-1; M is S or I; wherein when M=I, r=0, and when M=S, r=1 provided that at least one of g1 and g2≠0.

In addition, the present invention provides polymers comprising as polymerized units one or more of the photoacid generator compounds of formula (II) described above. Such polymers are useful as photoacid generator compounds in photoresist compositions.

Also provided by the present invention is a photoresist composition comprising any of the above described photoacid generator compounds.

Further, the present invention provides a method of forming a relief image comprising (a) applying a coating layer of a photoresist composition described above on a substrate; and (b) exposing the photoresist coating layer to patterned activating radiation and developing the exposed photoresist layer to provide a relief image. The relief images (e.g. a patterned line having essentially vertical sidewalls) can have sub-quarter micron dimensions or less, such as sub-0.2 or sub-0.1 micron dimensions.

As used herein, the term "alkyl" includes linear, branched and cyclic alkyl. As used herein, the term "fluoroalkyl" refers to an alkyl group having one or more of its hydrogens replaced with one or more fluorine atoms. Fluoroalkyl includes all amounts of fluorine substitution from monofluoroalkyl to perfluoroalkyl. The term "(meth)acrylate" includes both acrylate and methacrylate. Likewise, the term "(meth) acrylic" includes acrylic and methacrylic. The articles "a" and "an" refer to the singular and the plural. The following abbreviations shall have the following meanings: ° C.=degrees Celsius; nm=nanometers; μm=micron=micrometer; cm=centimeter; mJ=milliJoules; wt %=weight percent; and PAG=photoacid generator. All ratios are molar ration unless otherwise indicated.

As referred to herein, a base-reactive group will not react significantly (e.g. will not undergo a bond-breaking reaction) prior to a development step of the photoresist that comprises the base-reactive group. Thus, for instance, a base-reactive group will be substantially inert during pre-exposure soft-bake, exposure and post-exposure bake steps. By "substantially inert" it is meant that ≤5%, preferably ≤1%, of the base-reactive groups (or moieties) will decompose, cleave or react during the pre-exposure soft-bake, exposure and post-exposure bake steps. A base-reactive group as referred to herein will typically be reactive under typical photoresist development condition, e.g. single puddle development with 0.26N tetrabutyl ammonium hydroxide developer composition.

Preferred base-reactive groups of a component of photoacid generator compounds of the invention may provide upon treatment with base (such as aqueous alkaline developer) one or more hydroxy groups, one or more carboxylic acid groups, one or more sulfonic acid groups, and/or one or more other polar groups that will render the resist coating layer more hydrophilic.

While not being bound by any theory, it is believed that photoresists of the invention can exhibit reduced defects by providing a more hydrophilic surface of the photoresist relief image as a result of reaction of the base-reactive groups and production of more polar (hydrophilic) groups on the photoacid generator compound during the development step, which can reduce occurrence of defects, particularly organic material residues in substrates areas intended to be bared upon development. Without being bound by any theory, it is believed that photoacid generator compounds of the invention can address desired low diffusivity of PAG acid in the resist film as well as reduce after-develop defectivity. It is further believed that the photoresist compositions containing the present PAGs show improved exposure latitude (EL), and/or reduced mask error factor (MEF), compared to conventional photoresists.

The PAGs of the present invention have the formula (I) or (II)

$$R^5M^+R^6R^7{}_r-O_3S-R^1{}_p-X_y-(R^2Z_wR^3)_x \quad (I)$$

$$(P^g-R^4-Z^2)_{g1}R^5M^+R^6R^7{}_r-O_3S-R^1{}_p-X_y-(R^2Z_wR^3)_{x1}(R^2Z^1-R^4P^g)_{g2} \quad (II)$$

wherein each $R^1$ is chosen from $(C_1-C_{10})$alkyl, heteroatom-containing $(C_1-C_{10})$alkyl, fluoro$(C_1-C_{10})$alkyl, heteroatom-containing fluoro$(C_1-C_{10})$alkyl, $(C_6-C_{10})$aryl, and fluoro$(C_6-C_{10})$aryl; each $R^2$ is a chemical bond or a $(C_1-C_{30})$hydrocarbyl group; each $R^3$ is H or a $(C_1-C_{30})$hydrocarbyl group; each $R^4$ is a chemical bond or a $(C_1-C_{30})$hydrocarbyl group; $R^5$, $R^6$ and $R^7$ independently are chosen from an optionally substituted carbocylic aryl group, an allyl group, and an optionally substituted $(C_1-C_{20})$alkyl group; X is a chemical bond or a divalent linking group; Z is chosen from a β-heteroatom-substituted lactone, an acetoacetoxy ester, —C(O)—O—C(O)—$R^1$—, —C(CF$_3$)$_2$O—, —COO—$R^f$—, —SO$_3$—$R^f$—, —OCH$_{3-z}$(CH$_2$OC(=O)—$R^f$—)$_z$, and a $(C_5-C_{30})$cyclohydrocarbyl group comprising a base-reactive group; $Z^1$ is a divalent base-reactive group; $Z^2$ is chosen from a β-heteroatom-substituted lactone, —C(O)—O—C(O)—$R^1$—, an acetoacetoxy ester, —COO—$R^f$—, —SO$_3$—$R^f$—, —CH$_{3-z}$(CH$_2$OC(=O)—$R^f$—)$_z$, and a $(C_5-C_{30})$cyclohydrocarbyl group comprising a base-reactive group; each $R^f$ is independently a fluoro$(C_1-C_{10})$alkyl; $P^g$ is a polymerizable group; p=0-6; w=1-3; x=1-4; x1=0-4; y=0-5; z=1-2; g1=0-3; g2=0-3; r=0-1; M is S or I; wherein when M=I, r=0, and when M=S, r=1 provided that at least one of g1 and g2≠0.

Preferably, $R^1$ is $(CR^a{}_2)_n$, wherein each $R^a$ is chosen from H, F, $(C_1-C_{10})$alkyl and fluoro$(C_1-C_{10})$alkyl; and n=0-6, preferably 0-4, and more preferably 1-4. It is more preferred that $R^a$ is chosen from H, F, fluoro$(C_1-C_{10})$alkyl, yet more preferably H, F, and fluoro$(C_1-C_6)$alkyl, and even more preferably F, and fluoro$(C_1-C_6)$alkyl.

$R^3$ may be any suitable $(C_1-C_{30})$hydrocarbyl group. Exemplary hydrocarbyl groups include $(C_1-C_{30})$alkyl, fluoro$(C_1-C_{30})$alkyl and $(C_6-C_{20})$aryl. It is preferred $R^3$ is chosen from H, $(C_1-C_{30})$alkyl, fluoro$(C_1-C_{30})$alkyl and $(C_6-C_{20})$aryl.

$R^4$ may be any suitable $(C_1-C_{30})$hydrocarbyl group. Exemplary hydrocarbyl groups include $(C_1-C_{30})$alkyl, fluoro$(C_1-C_{30})$alkyl and $(C_6-C_{20})$aryl. It is preferred $R^4$ is chosen from a chemical bond, $(C_1-C_{30})$alkyl, fluoro$(C_1-C_{30})$alkyl and $(C_6-C_{20})$aryl.

X is preferably a divalent linking group. wide variety of divalent linking groups may be used for X. Exemplary divalent linking groups include $C_1-C_{30}$-containing groups, preferably those having one or more heteroatoms chosen from O, N, S, and combinations thereof. Other suitable divalent linking groups are heteroatom-containing functional groups, such as those of the formula —$X^2{}_{t1}$—$(Y^2$=$X^3)X^3{}_{t2}$—, wherein $X^2$=O, S, or NR; $Y^2$=C, S, or S=O, $X^3$=O or S; t1=0 or 1; and t2=0 or 1. Preferred divalent linking groups include any divalent group having one or more of the following: —C(O)O—, —C(O)S—, —SO$_3$—, —S(O)—, —SO$_2$—,

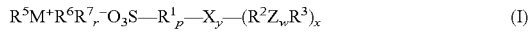
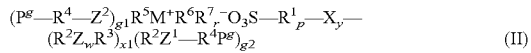

and combinations thereof.

The present PAGs comprise one or more base-reactive moieties, that is Z in formula (I) and $Z^1$ or $Z^2$ in formula (II).

In formula (I), Z represents a base-reactive group. Such base-reactive group may be bonded to a $(C_1-C_{10})$hydrocarbyl group, such as when Z is an anhydride. When such hydrocarbyl group is present, it is preferably chosen from $(C_1-C_{10})$alkyl, heteroatom-containing $(C_1-C_{10})$alkyl, fluoro$(C_1-C_{10})$alkyl, heteroatom-containing fluoro$(C_1-C_{10})$alkyl, $(C_6-C_{10})$aryl, and fluoro$(C_6-C_{10})$aryl. It is preferred that Z is chosen from a β-heteroatom-substituted lactone, —C(CF$_3$)$_2$O—, —COO—$R^f$—, —SO$_3$—$R^f$—, —CH$_{3-z}$(CH$_2$OC(=O)—$R^f$—)$_z$, and a $(C_5-C_{30})$cyclohydrocarbyl group comprising a base-reactive group. More preferably, Z is chosen from a β-heteroatom-substituted lactone, —C(CF$_3$)$_2$O—, —COO—$R^f$—, —SO$_3$—$R^f$—, and —CH$_{3-z}$(CH$_2$OC(=O)—$R^f$—)$_z$. It is preferred that z=1 or 2. Preferably, $R^f$=fluoro$(C_1-C_8)$alkyl. It is further preferred that $R^f$=fluoro$(C_1-C_8)$alkyl and z=1 or 2. Exemplary β-heteroatom-substituted lactones include, without limitation, those of the following formulas:

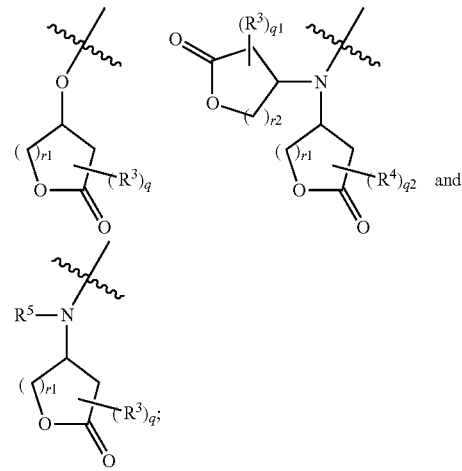

wherein r1 and r2 are independently 1-10; q1 and q2 are independently 1-10; $R^3$ and $R^4$ are independently chosen from $(C_1-C_{10})$hydrocarbyl, $R^5$ is H or $(C_1-C_{10})$hydrocarbyl. Preferred β-heteroatom-substituted lactones include the following:

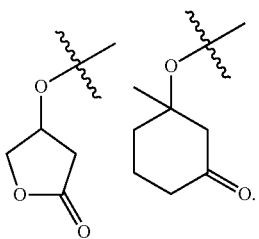

The group —COO—R$^f$— includes both —C(O)—O—R$^f$— and —O—C(O)—R$^f$—. Likewise, the group —SO$_3$—R$^f$— includes both —SO$_2$—O—R$^f$— and —O—S(O$_2$)—R$^f$—. The (C$_5$-C$_{30}$)cyclohydrocarbyl groups comprising a base-reactive group may be aromatic or aliphatic, and may optionally contain or more heteroatoms chosen from O, S and N. Exemplary base-reactive groups in such (C$_5$-C$_{30}$)cyclohydrocarbyl groups include hydroxyl, fluoroalkyl esters, fluorosulfonate esters, and —C(CF$_3$)$_2$O—. Preferred (C$_5$-C$_{30}$)cyclohydrocarbyl groups comprising a base-reactive group are phenol, and hydroxynaphthylene.

Z$^1$ may be any suitable base reactive group, which is polyvalent. Polyvalent refers to a base-reactive group bonded to two other group (divalent) or more than two. Preferably, Z$^1$ is a divalent base-reactive group. Exemplary base-reactive groups for Z$^1$ include β-heteroatom-substituted lactone, an acetoacetoxy ester, —C(O)—O—C(O)—R$^1$—; —COO—R$^f$—, —SO$_3$—R$^f$—, —CH$_{3-z}$(CH$_2$OC(=O)—R$^f$—)$_z$, a (C$_5$-C$_{30}$)cyclohydrocarbyl group comprising a base-reactive group, —COOR$^1$—, —SO$_3$R$^1$—,

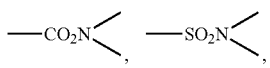

and combinations thereof, wherein R$^1$, R$^f$ and z are as defined above. Preferably, Z$^1$ is chosen from β-heteroatom-substituted lactone, an acetoacetoxy ester, —C(O)—O—C(O)—R$^1$—; —COO—R$^f$—, —SO$_3$—R$^f$—, —CH$_{3-z}$(CH$_2$OC(=O)—R$^f$—)$_z$, and a (C$_5$-C$_{30}$)cyclohydrocarbyl group comprising a base-reactive group, and more preferably Z$^1$ is chosen from β-heteroatom-substituted lactone, an acetoacetoxy ester, —C(O)—O—C(O)—R$^1$—; —COO—R$^f$—, —SO$_3$—R$^f$—, and —CH$_{3-z}$(CH$_2$OC(=O)—R$^f$—)$_z$. Exemplary β-heteroatom-substituted lactones are those described above for Z. Suitable (C$_5$-C$_{30}$)cyclohydrocarbyl groups comprising a base-reactive group are those described above for Z.

Z$^2$ is also a polyvalent (includes divalent) base-reactive group and is chosen from a β-heteroatom-substituted lactone, —C(O)—O—C(O)—R$^1$—, an acetoacetoxy ester, —COO—R$^f$—, —SO$_3$—R$^f$—, —CH$_{3-z}$(CH$_2$OC(=O)—R$^f$—)$_z$, and a (C$_5$-C$_{30}$)cyclohydrocarbyl group comprising a base-reactive group, wherein R$^1$, R$^f$ and z are as defined above. Preferred groups for Z$^2$ are a β-heteroatom-substituted lactone, —C(O)—O—C(O)—R$^1$—, —COO—R$^f$—, —SO$_3$—R$^f$—, —CH$_{3-z}$(CH$_2$OC(=O)—R$^f$—)$_z$, and a (C$_5$-C$_{30}$)cyclohydrocarbyl group comprising a base-reactive group, and more preferably a β-heteroatom-substituted lactone, —C(O)—O—C(O)—R$^1$—, —COO—R$^f$—, —SO$_3$—R$^f$—, and —CH$_{3-z}$(CH$_2$OC(=O)—R$^f$—)$_z$. Exemplary β-heteroatom-substituted lactones are those described above for Z. Suitable (C$_5$-C$_{30}$)cyclohydrocarbyl groups comprising a base-reactive group are those described above for Z.

In the compounds of formula (II), P$^g$ may be any suitable polymerizable group. The term "polymerizable group" means any group which may be polymerized by itself (homopolymerization) or with one or more other polymerizable groups (copolymerization) to form a polymer. It is preferred that P$^g$ be a group that can be polymerized by either free-radical polymerization or by condensation. A free-radical polymerizable group is preferred, and more preferably P$^g$ comprises a (meth)acrylic group or a vinyl group.

In the compound of formula (II), at least one of g1 and g2≠0, that is, at least one polymerizable group attached to a base-reactive group (either Z$^1$ or Z$^2$) must be present. It is preferred that either g1 or g2=1.

It is preferred that M is an organic sulfonium cation. Suitable cations for M are sulfonium cations of formula (III) and iodonum cations of formula (IV):

wherein R$^5$ to R$^7$ independently represents a carbocylic aryl group which may contain a substituent group (that is, may be optionally substituted), an allyl group, a (C$_1$-C$_{20}$)alkyl group which may contain a substituent group (that is may be optionally substituted) such as a perfluoro(C$_1$-C$_{20}$)alkyl group or a (C$_6$-C$_{15}$)aralkyl group such as benzyl and phenethyl, preferably at least one of R$^5$ to R$^7$ represents a carbocyclic aryl group; alternatively, R$^5$ and R$^6$, or R$^6$ and R$^7$ are mutually bonded to form a ring together with the sulfur ion to which they are attached, R$^7$ represents a carbocyclic aryl group which may contain a substituent group (that is, may be optionally substituted), a C$_1$-C$_{20}$)alkyl group which may contain a substituent group (that is, may be optionally substituted).

Preferred sulfonium cations are those of formulae (3a) to (3f):

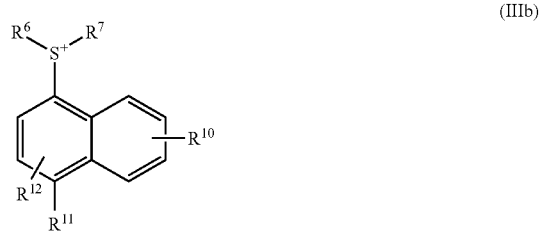

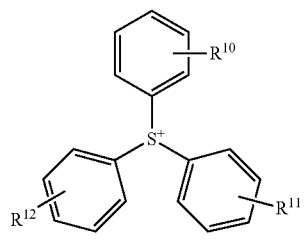
(IIIc)

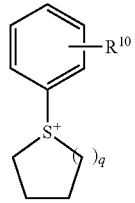
(IIId)

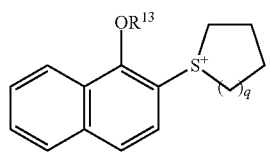
(IIIe)

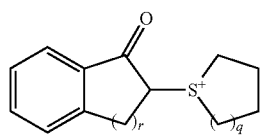
(IIIf)

wherein $R^6$ and $R^7$ are as described above for formula (3); $R^{10}$ to $R^{12}$ are independently chosen from hydrogen, hydroxy, $(C_1-C_{20})$alkyl group, halogen, $(C_1-C_{20})$alkoxy group, aryl, thiophenoxy, thio$(C_1-C_{20})$alkoxy group and $(C_1-C_{20})$alkoxycarbonyl; $R^{13}$ is a $(C_1-C_{20})$alkyl; q=1-10; and r=1-2. Each of $R^{10}$ to $R^{12}$ may independently contain an acid labile group, a base labile group or a base soluble group.

Particularly preferred sulfonium cations of formula (3c) are shown by structures C1-C6, particularly suitable sulfonium cations of formula (3d) are shown by structures D1 and D2, and a particularly suitable structure of formula (3e) is shown by structure E1.

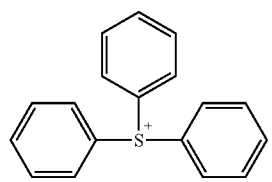
C1

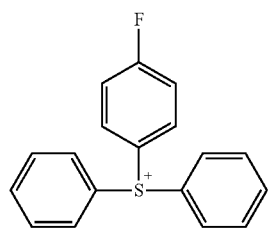
C2

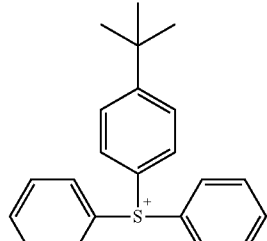
C3

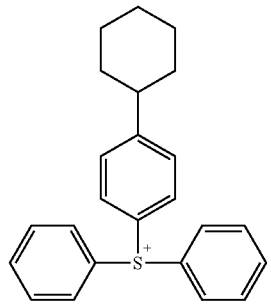
C4

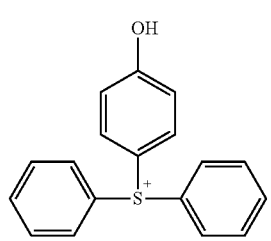
C5

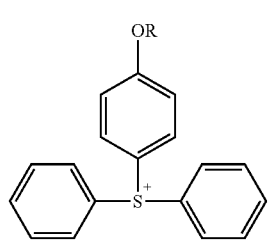
C6

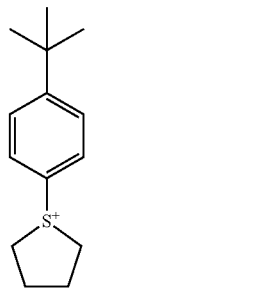
D1

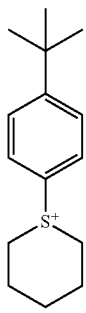
D2

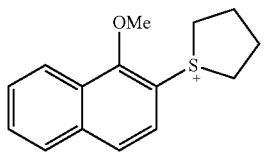
E1

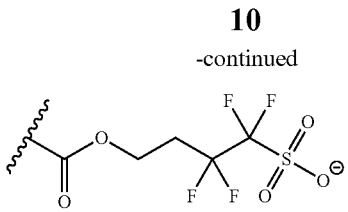
Structure 5

These adamantine components can be substituted with other bulky cage structures such as norbornane or dinorbornane that contain alcohol or carboxylic acid groups to incorporate the alkali-cleavable unit.

Other preferred compounds of formula (I) are shown in Structure 6 and 7.

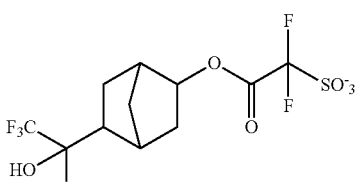
Structure 6

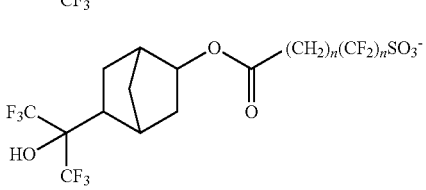
Structure 7

In the case of polymers comprising as polymerized units the PAGs of formula (II), either or both anion and cation components may be covalently tethered to the resin. Such polymers may be prepared according to known procedures.

Suitable PAGs of formula (II) may comprise structures as follows:

When g1=1, the compounds of formula (II) comprise at least one polymerizable group ($P^g$) bonded to a base-reactive group, which is itself bonded to $R^5$. When g1=0, then g2 must be ≥1. Likewise, when g2=0, g1 must ≥1.

The present PAGs may comprise one or more than one base-reactive group as described above. In certain aspects, preferred are ionic photoacid generator compounds, particularly PAG compounds generate a sulfonic acid ($-SO_3^-$) upon photoactiviation. In an especially preferred aspect, fluorinated PAGs are provided that comprises one or more base-reactive groups. Particularly preferred are fluorinated PAGs with one or more base-reactive groups that generate a sulfonic acid ($-SO_3^-$) upon photoactiviation, such as any of the following groups: a fluorinated sulfonic acid group (e.g. $-CF_2SO_3^-$, $-CHFSO_3^-$, -(ester)$CF_2SO_3^-$, and -(ester)$CHFSO_3^-$.

Some specifically preferred compounds of formula (I) include adamantane compounds of the following formula:

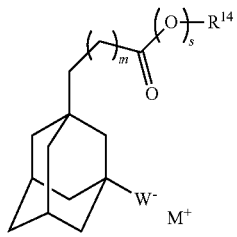

wherein $R^{14}$ is chosen from H, F, ($C_1$-$C_{10}$)alkyl and fluoro (C1-C10)alkyl; W=a fluorinated sulfonic acid moiety; m=0-5, and s=0 or 1; provided that when s=1, m=0. It is preferred that W is chosen from Structures 4 and 5.

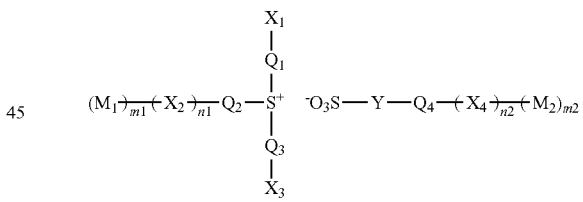

wherein at least one of $M_1$ and $M_2$ are polymerizable group; $X_{1-4}$ represent base-reactive group; Y represents fluorinated linker; $Q_{1-4}$ represent divalent group; each of n1 and n2 represent an integer of 0 or 1, and n1≠n2; m1 and m2 represent an integer of 0 or 1, and m1≠m2.

Other suitable PAGs of formula (II) are shown by structures (A) and (B)

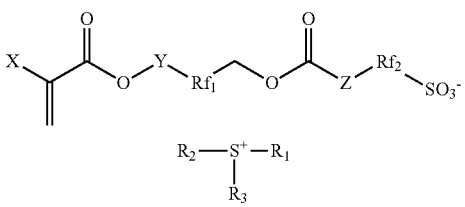
(A)

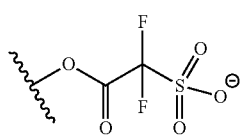
Structure 4

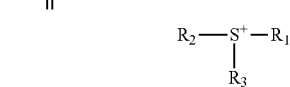

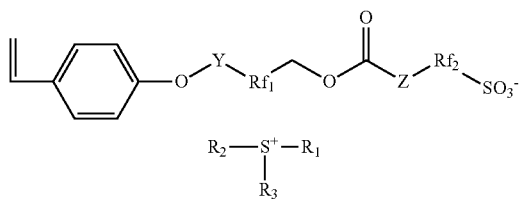

wherein $R_1$, $R_2$ and $R_3$ are each independently a substituted or unsubstituted, straight or branched $(C_1-C_{10})$alkyl, alkenyl or oxoalkyl group, or a substituted or unsubstituted $(C_6-C_{18})$ aryl, alkyl or aryloxoalkyl group, or any two or more of $R_1$, $R_2$ and $R_3$ may be bonded together to form a ring with the sulfur atom; $R_{f1}$ and $R_{f2}$ are perfluorinated or partially fluorinated, substituted or unsubstituted, straight or branched $(C_1-C_{10})$ alkyl group or cyclic alkyl groups; X is H, $CH_3$, F, $CF_3$ or other substitutes; Y and Z is substituted or unsubstituted, straight or branched $(C_1-C_{20})$alkyl, cyclic alkyl and/or caged group linkage.

Preferably, PAGs of the invention are used in positive-acting or negative-acting chemically amplified photoresists, i.e. negative-acting resist compositions which undergo a photoacid-promoted crosslinking reaction to render exposed regions of a coating layer of the resist less developer soluble than unexposed regions, and positive-acting resist compositions which undergo a photoacid-promoted deprotection reaction of acid labile groups of one or more composition components to render exposed regions of a coating layer of the resist more soluble in an aqueous developer than unexposed regions.

Photoresists of the invention contain an imaging-effective amount of one or more of the present PAGs. Such PAGs may be a separate component, or may be bound to the resin. In yet a further alternative, photoresists of the invention may comprise both an imaging-effective amount of one or more of the individual PAGs and one or more resins comprising one or more of the present PAGs as polymerized units. Resists of the invention also may comprise a mixture of distinct PAGs, typically a mixture of 2 or 3 different PAGs, more typically a mixture that consists of a total of 2 distinct PAGs. At least one PAG of the mixture have one or more base-cleavable groups as disclosed herein.

Photoresists of the invention typically comprise a resin binder (polymer), a PAG as described above, and optionally one or more other components such as a base (quencher), solvent, actinic and contrast dyes, anti-striation agents, plasticizers, speed enhancers, sensitizers, and the like. More than one of any of these photoresist components may be used. Such optional additives if used are typically present in the composition in minor amounts such as from 0.1 to 10 wt % based on total solids of the photoresist composition. Preferably the resin binder has functional groups that impart alkaline aqueous developability to the photoresist composition. For example, preferred are resin binders that comprise polar functional groups such as hydroxyl or carboxylate. Preferably the resin binder is used in a resist composition in an amount sufficient to render the resist developable with an aqueous alkaline solution.

Preferred resins that have acid-labile deblocking groups for use in a positive-acting chemically-amplified photoresist of the invention have been disclosed in European Pat. App. No. 0829766 (resins with acetal and ketal resins) and European Pat. App. No. EP 0783136 (terpolymers and other copolymers including units of 1) styrene; 2) hydroxystyrene; and 3) acid labile groups, particularly alkyl acrylate acid labile groups such as t-butylacrylate or t-butylmethacrylate). In general, resins having a variety of acid labile groups will be suitable, such as acid sensitive esters, carbonates, ethers, imides, etc. The photoacid labile groups will more typically be pendant from a polymer backbone, although resins that have acid labile groups that are integral to the polymer backbone also may be employed.

Preferred imaging wavelengths of the photoresists of the invention include sub-300 nm wavelengths, such as 248 nm, and more preferably sub-200 nm wavelengths, such as 193 nm and EUV, although other sub-200 nm wavelengths may be used, such as electron beam, ion beam and x-ray, or other ionizing radiation.

For imaging at wavelengths greater than 200 nm, such as 248 nm, phenolic resins are typically preferred. Preferred phenolic resins are poly(vinylphenols) which may be formed by block polymerization, emulsion polymerization or solution polymerization of the corresponding monomers in the presence of a catalyst. Particularly preferred resins useful for imaging at these wavelengths include: i) polymers that contain polymerized units of a vinyl phenol and an alkyl (meth) acrylate, where the polymerized alkyl (meth)acrylate units can undergo a deblocking reaction in the presence of photoacid. Exemplary alkyl (meth)acrylates that can undergo a photoacid-induced deblocking reaction include e.g. t-butyl acrylate, t-butyl methacrylate, methyladamantyl acrylate, methyl adamantyl methacrylate, and other non-cyclic alkyl and alicyclic acrylates that can undergo a photoacid-induced reaction, such as polymers in U.S. Pat. Nos. 6,042,997 and 5,492,793, incorporated herein by reference; ii) polymers that contain polymerized units of a vinyl phenol, an optionally substituted vinyl phenyl (e.g. styrene) that does not contain a hydroxy or carboxy ring substituent, and an alkyl (meth) acrylate such as those deblocking groups described with polymers i) above, such as polymers described in U.S. Pat. No. 6,042,997, incorporated herein by reference; and iii) polymers that contain repeat units that comprise an acetal or ketal moiety that will react with photoacid, and optionally aromatic repeat units such as phenyl or phenolic groups.

Resins suitable for imaging at sub-200 nm, such as at 193 nm, include various (meth)acrylate monomers and are well known in the art, such as those disclosed in U.S. Pat. Nos. 7,968,268, 7,700,256; 7,432,035; 7,122,589; 7,041,838; 6,492,091; 6,280,898; and 6,239,231, and U.S. Pat. Pub. Nos. 2009/0117489 and 2011/0003257. Exemplary resins include those comprising units of the following general formulae (I), (II) and (III):

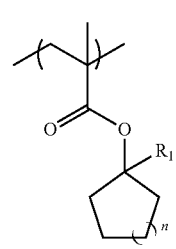

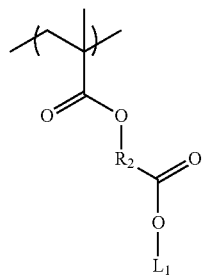
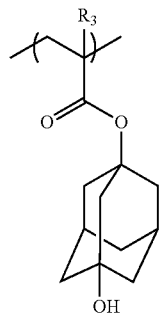

wherein: $R_1$ is a $(C_1-C_3)$alkyl group; $R_2$ is a $(C_1-C_3)$alkylene group; $L_1$ is a lactone group; and n is 1 or 2.

Suitable monomers for forming units of formula (I) include, for example, the following:

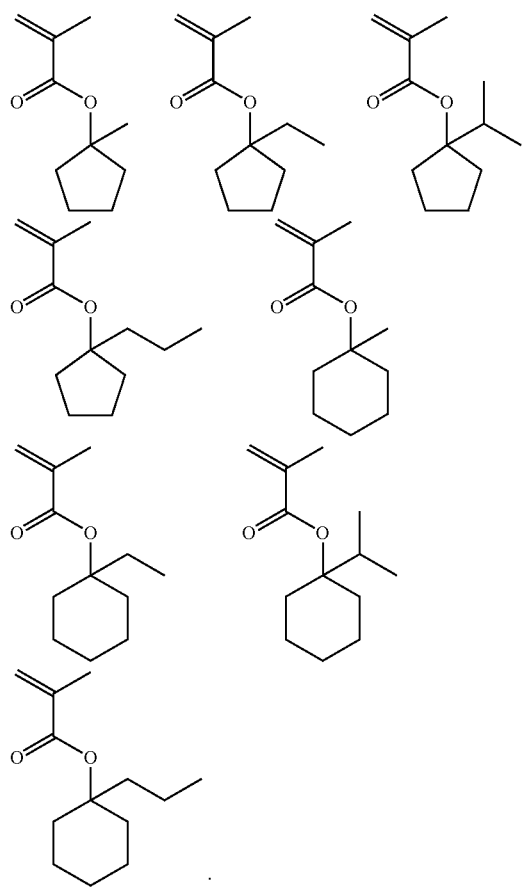

Suitable monomers for forming units of general formula (II) include, for example, the following:

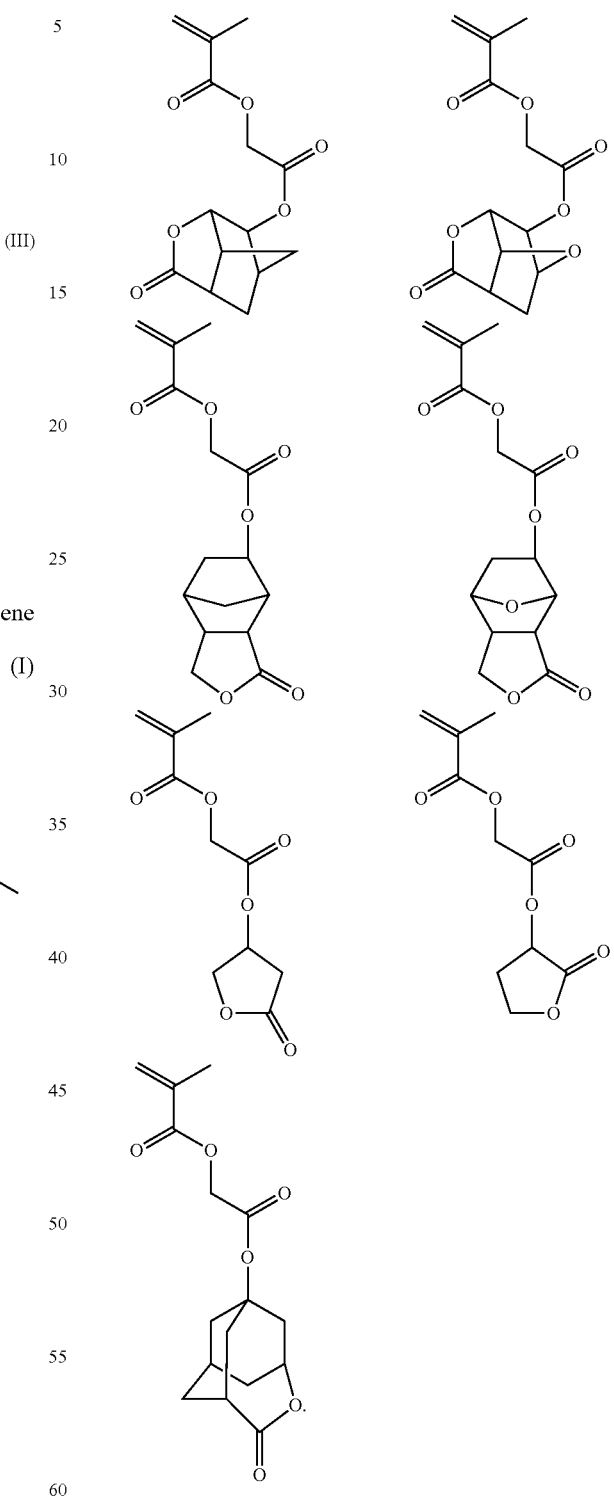

Monomers for forming the unit of formula (III) include 3-hydroxy-1-adamantyl methacrylate (HAMA) and preferably 3-hydroxy-1-adamantyl acrylate (HADA).

The resin can include one or more additional units of general formulae (I), (II) and/or (III) different from the first units. Where additional such units are present in the resin, they will preferably include an additional leaving group-containing unit of formula (I) and/or a lactone-containing unit of formula (II).

In addition to the polymerized units described above, the resin can include one or more additional monomer units which are not of general formula (I), (II) or (III). A wide variety of such additional monomer units may be used to prepare photoresist resins useful in the present invention. Typically, the additional units for the resin will include the same or similar polymerizable group as those used for the monomers used to form the units of general formula (I), (II) or (III), but may include other, different polymerizable groups in the same polymer backbone, such as those which contain polymerized units of vinyl or a non-aromatic cyclic olefin (endocyclic double bond) such as an optionally substituted norbornene. For imaging at sub-200 nm wavelengths such as 193 nm, the resin is typically substantially free (that is, less than 15 mole %) of phenyl, benzyl or other aromatic groups where such groups are highly absorbing of the radiation. The additional units if used are typically present in the polymer in an amount of from 10 to 30 mol %.

Blends of two or more resins can be used in the compositions of the invention. The resin is present in the resist composition in an amount sufficient to obtain a uniform coating of desired thickness. Typically, the resin is present in the composition in an amount of from 70 to 95 wt % based on total solids of the photoresist composition. Because of improved dissolution properties of the resin in organic developers, useful molecular weights for the resin are not limited to lower values, but cover a very broad range. For example, the weight average molecular weight $M_w$ of the polymers is typically less than 100,000, for example, from 5000 to 50,000, more typically from 6000 to 30,000 or from 7,000 to 25,000.

Suitable monomers used in forming the resins are commercially available and/or can be synthesized using known methods. The resins can readily be synthesized by persons skilled in the art using the monomers with known methods and other commercially available starting materials.

A preferred optional additive of photoresists of the invention is an added base, particularly tetrabutylammonium hydroxide (TBAH) or various amides, which can enhance resolution of a developed resist relief image. The added base is suitably used in relatively small amounts, e.g. 1 to 10 wt % relative to the PAG, more typically 1 to 5 wt %. Other preferred basic additives include ammonium sulfonate salts such as piperidinium p-toluenesulfonate and dicyclohexylammonium p-toluenesulfonate; alkyl amines such as tripropylamine and dodecylamine; aryl amines such as diphenylamine, triphenylamine, aminophenol, 2-(4-aminophenyl)-2-(4-hydroxyphenyl)propane, etc.

The present photoresist compositions typically comprise a solvent. Suitable solvents include, for example: glycol ethers such as 2-methoxyethyl ether (diglyme), ethylene glycol monomethyl ether, and propylene glycol monomethyl ether; propylene glycol monomethyl ether acetate; lactates such as methyl lactate and ethyl lactate; propionates such as methyl propionate, ethyl propionate, ethyl ethoxy propionate and methyl-2-hydroxy isobutyrate; Cellosolve esters such as methyl Cellosolve acetate; aromatic hydrocarbons such as toluene and xylene; and ketones such as acetone, methylethyl ketone, cyclohexanone and 2-heptanone. A blend of solvents such as a blend of two, three or more of the solvents described above also are suitable. The solvent is typically present in the composition in an amount of from 90 to 99 wt %, more typically from 95 to 98 wt %, based on the total weight of the photoresist composition.

The photoresists of the invention are generally prepared following known procedures. For example, a resist of the invention can be prepared as a coating composition by dissolving the components of the photoresist in a suitable solvent. The resin binder component of resists of the invention are typically used in an amount sufficient to render an exposed coating layer of the resist developable such as with an aqueous alkaline solution. More particularly, a resin binder will suitably comprise 50 to 90 wt % of total solids of the resist. The photoactive component should be present in an amount sufficient to enable generation of a latent image in a coating layer of the resist. More specifically, the photoactive component will suitably be present in an amount of from 1 to 40 wt % of total solids of a resist. Typically, lesser amounts of the photoactive component will be suitable for chemically amplified resists.

The desired total solids content of the present photoresist compositions will depend on factors such as the particular polymers in the composition, final layer thickness and exposure wavelength. Typically the solids content of the photoresist varies from 1 to 10 wt %, more typically from 2 to 5 wt %, based on the total weight of the photoresist composition.

Preferred negative-acting photoresist compositions of the invention comprise a mixture of materials that will cure, crosslink or harden upon exposure to acid, and a photoactive component of the invention. Preferred negative acting compositions comprise a resin binder such as a phenolic or non-aromatic resin, a crosslinker component and a photoactive component of the invention. Such compositions and the use thereof has been disclosed in European Patent Applications EP 0164248 and EP 0232972 and in U.S. Pat. No. 5,128,232 to Thackeray et al. Preferred phenolic resins for use as the resin binder component include novolaks and poly(vinylphenol)s such as those discussed above. Preferred crosslinkers include amine-based materials, including melamine, glycolurils, benzoguanamine-based materials and urea-based materials. Melamine-formaldehyde resins are generally most preferred. Such crosslinkers are commercially available, e.g. the melamine resins sold by Cytec under the trade names Cymel 300, 301 and 303. Glycoluril resins are sold by Cytec under trade names Cymel 1170, 1171, 1172, urea-based resins are sold under the trade names of Beetle 60, 65 and 80, and benzoguanamine resins are sold under the trade names Cymel 1123 and 1125.

The photoresists of the invention can be used in accordance with known procedures. Though the photoresists of the invention may be applied as a dry film, they are preferably applied on a substrate as a liquid coating composition, dried by heating to remove solvent preferably until the coating layer is tack free, exposed through a photomask to activating radiation, optionally post-exposure baked to create or enhance solubility differences between exposed and nonexposed regions of the resist coating layer, and then developed preferably with an aqueous alkaline developer to form a relief image. The substrate on which a resist of the invention is applied and processed suitably can be any substrate used in processes involving photoresists such as a microelectronic wafer. For example, the substrate can be a silicon, silicon dioxide or aluminum-aluminum oxide microelectronic wafer. Gallium arsenide, ceramic, quartz or copper substrates may also be employed. Printed circuit board substrates such as copper clad laminates are also suitable substrates. Substrates used for liquid crystal display and other flat panel display applications are also suitably employed, e.g. glass substrates, indium tin oxide coated substrates and the like. A liquid coating resist composition may be applied by any standard means such as spinning, dipping or roller coating.

The photoresist layer (with overcoated barrier composition layer, if present) may be preferably exposed to activating radiation in an immersion lithography system, i.e. where the space between the exposure tool (particularly the projection lens) and the photoresist coated substrate is occupied by an immersion fluid, such as water or water mixed with one or more additives such as cesium sulfate, which can provide a fluid of enhanced refractive index. Preferably the immersion fluid (e.g., water) has been treated to avoid bubbles, e.g. water can be degassed to avoid nanobubbles. References herein to "immersion exposing" or other similar term indicates that exposure is conducted with such a fluid layer (e.g., water or water with additives) interposed between an exposure tool and the coated photoresist composition layer.

The exposure energy should be sufficient to effectively activate the photoactive component of the radiation sensitive system to produce a patterned image in the resist coating layer. Suitable exposure energies typically range from about 1 to 300 mJ/cm$^2$. Suitable post-exposure bake temperatures are from 50° C. or greater, more specifically from 50 to 140° C. For an acid-hardening negative-acting resist, a post-development bake may be employed if desired at temperatures of from 100 to 150° C. for several minutes or longer to further cure the relief image formed upon development. After development and any post-development cure, the substrate surface bared by development may then be selectively processed, for example chemically etching or plating substrate areas bared of photoresist in accordance with procedures known in the art. Suitable etchants include a hydrofluoric acid etching solution and a plasma gas etch such as an oxygen plasma etch.

The invention also provide methods for forming relief images of the photoresists of the invention, including methods for forming highly resolved patterned photoresist images (for example, a patterned line having essentially vertical sidewalls) of sub-quarter μm dimensions or less, such as sub-0.2 or sub-0.1 μm dimensions.

The invention further provides articles of manufacture comprising substrates such as a microelectronic wafer or a flat panel display substrate having coated thereon the photoresists and relief images of the invention.

EXAMPLE 1

The photoacid generator TPS NBHFA-TFPS was prepared by a multi-step synthesis as outlined in Scheme 1 and the following paragraphs. The detailed synthetic process is presented below.

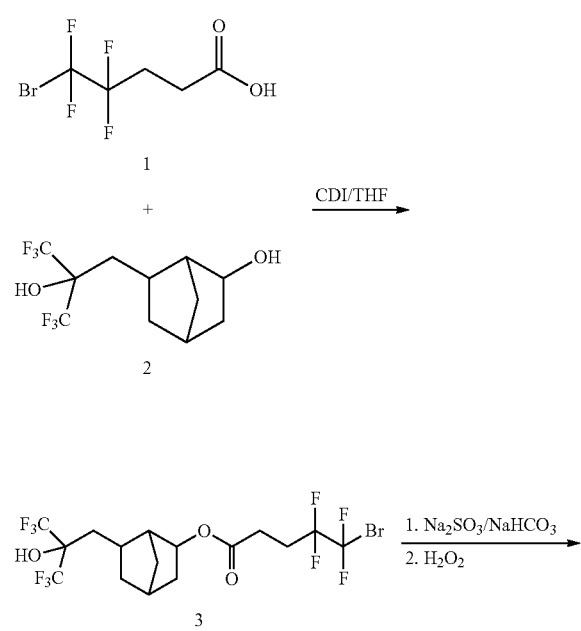

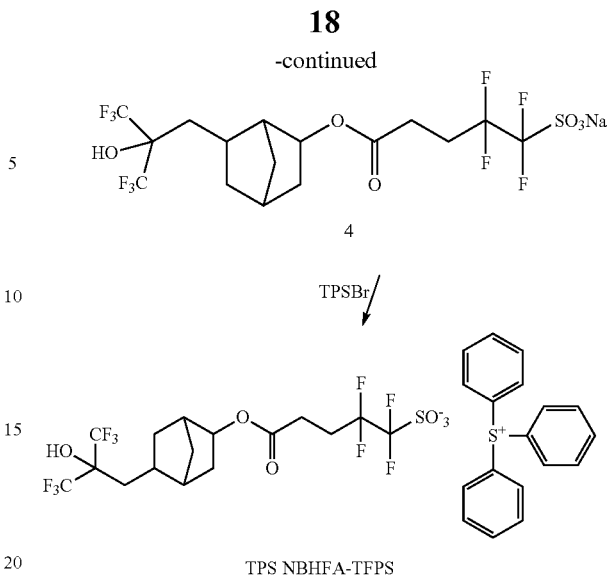

TPS NBHFA-TFPS

To a solution of 4-bromo-3,3,4,4-tetrafluorobutanoic acid (1, 26 g, 102.7 mmol) in 150 mL tetrahydrofuran was added carbonyldiimidazole (CDI, 16.7 g, 103.0 mmol) and the mixture was stirred at room temperature for 2 hours. The reaction mixture was heated up to 70° C. and then compound 2 (30 g, 102.6 mmol) was added and the reaction was stirred at 70° C. under nitrogen for 16 hours. The solvent was removed under reduced pressure and the resulting oily residue was dissolved in 200 mL methylene chloride. The later solution was washed twice with 200 mL 1 N HCl, washed once with 200 mL water, dried over MgSO$_4$ and the solvent removed under reduced pressure to produce compound 3 as colorless oil.

In the second step, compound 3 (45 g, 85.35 mmol) was dissolved in 200 mL acetonitrile. Sodium dithionite (32.69 g, 187.75 mmol) and sodium bicarbonate (21.5 g, 255.9 mmol) were dissolved in 200 mL deionized water. The aqueous solution was added to the stirred acetonitrile solution and the reaction mixture was stirred at 70° C. for 16 hours. Reaction monitoring by $^{19}$F NMR indicated complete conversion. The acetonitrile solution was used in the oxidation step without further isolation of the intermediary product. To the acetonitrile solution was added 100 mL water, Na$_2$WO$_4$.2H$_2$O (50 mg) followed by H$_2$O$_2$ (30 w/w % aqueous, 14.5 g). The reaction was stirred at ambient temperature for 16 hours. The organic phase was evaporated on the rotary evaporator. The residual solid was dissolved in 100 mL of acetone, and the solution was poured slowly into methyl t-butylether (2 L). A waxy product obtained which was isolated by removing the solvents by decantation. The waxy product was further dried under reduced pressure. The overall yield for the crude product 4 was 30.0 g (64%). The product was used in the next step without further purification.

In the last step, to a stirred mixture of 200 mL dichloromethane and 200 mL deionized water was added the crude compound 4 (30 g, 54.5 mmol) and triphenylsulfonium bromide (18.71 g, 54.5 mmol). The reaction was stirred at ambient temperature overnight. The phases were separated. The organic phase was washed five times with 200 mL volumes of deionized water. The organic phase was separated. The separated organic phase was concentrated and poured into methyl t-butyl ether to produce the target photoacid generator TPS NBHFA-TFPS.

EXAMPLE 2

Lithographic Evaluation

Photoacid generator compound TPS NBHFA-TFPS from Example 1 was evaluated lithographically, and compared conventional PAG, triphenylsulfonium perfluorobutane sulfonate. The photoresists were formulated using the components and proportions described below.

A photoresist polymer (A1) for use in the lithographic evaluations (below) was prepared using monomers M1-M5 below, according to the following procedure.

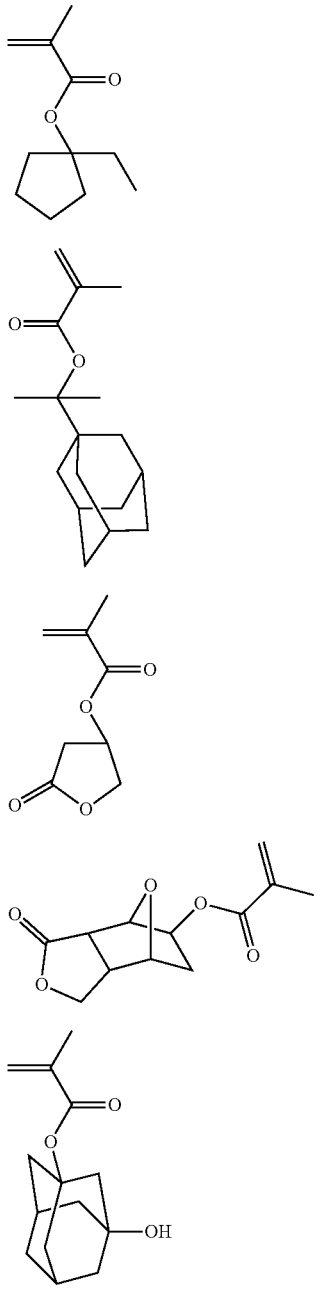

A solution of 1-ethylcyclopentyl methacrylate (ECPMA, M1; 20 mmol), 1-isopropyl-adamantanyl methacrylate (IAM, M2; 20 mmol), 2-oxo-tetrahydro-furan-3-ylmethacrylate (α-GBLMA, M3; 30 mmol), 3-oxo-4,10-dioxa-tricyclo[5.2.1.0²,⁶]dec-8(or 9)-yl methacrylate (ODOTMA, M4; 20 mmol), and 3-hydroxy-adamantanyl methacrylate (HAMA, M5; 10 mmol) dissolved in 30 g of tetrahydrofuran (THF) was degassed by bubbling with nitrogen and charged to a 500 mL flask equipped with a condenser, nitrogen inlet and mechanical stirrer along with an additional 10 g of degassed THF. The solution was brought to reflux, and 6 g of dimethyl-2,2-azodiisobutyrate dissolved in 5 g of THF was charged to the flask. The polymerization mixture was then stirred for about 4 hours at reflux, after which time the reaction was diluted with 5 g of THF and the polymerization mixture cooled to room temperature. The polymer was precipitated by addition to 1.0 L of isopropanol, collected by filtration, re-precipitated by dissolving in 50 g THF and addition to another 1.0 L isopropanol, and collected and dried under vacuum at 45° C. for 48 hours to yield photoresist polymer poly(IAM/ECPMA/α-GBLMA/ODOTMA/HAMA). Mw=8,000.

The photoresists were formulated using the components and proportions shown in Table 1, where the weight percentages were based on the total solids content of the composition. The base used was t-butyloxycarbonyl-4-hydroxypyridine (TBOC-4HP), and SLA (surface leveling agent or surfactant) was PF 656, available from Omnova. The photoresists were further formulated using as solvents propylene glycol methyl ether acetate (S1) and methyl 2-hydroxyisobutyrate (S2) in a 1:1 ratio by weight. The photoresist and comparative photoresist were each diluted to a final solids of 4 wt %.

TABLE 1

| Example | Polymer (wt %) | PAG | PAG (wt %) | Base (wt %) | SLA (wt %) |
|---|---|---|---|---|---|
| CEx. 1 | 89.29 | Triphenylsulfonium perfluorobutane sulfonate | 9.58 | 1.03 | 0.10 |
| Ex. 1 | 88.804 | TPS NBHFA-TFPS | 13.47 | 1.029 | 0.10 |

Photoresists from Example 1 and Comparative Example 1 were lithographically processed as follows. The photoresist was spin coated onto a 200 mm silicon wafer having an organic antireflective coating (AR™ 77, Dow Electronic Materials) and baked at 110° C. for 60 seconds, to form a resist film 100 nm in thickness. The photoresist was exposed with ArF excimer laser radiation (193 nm) using an ASML/1100 exposure tool (manufactured by ASML) with a numerical aperture (NA) of 0.75, under annular illumination with outer/inner sigma of 0.89/0.64 and focus offset/step 0.10/0.05. A line-space pattern mask targeting a linewidth of 90 nm and a pitch of 180 nm was used to image the features.

The patterned resist was post exposure baked (PEB) at 100° C. for 60 seconds followed by development with 0.26N aqueous tetramethylammonium hydroxide (TMAH) solution and subsequent water wash. For each example, an L/S pattern having a line width of 90 nm and a pitch of 180 nm was formed. Mask Error Factor (MEF) and Exposure Latitude (EL) were determined by top-down scanning electron microscopy (SEM) using images captured with a Hitachi 9380 CD-SEM, operating at an accelerating voltage of 800 volts (V), a probe current of 8.0 picoamperes (pA), and 200 Kx magnification. Exposure latitude (EL) was defined as a difference in exposure energy to print +/−10% of the target diameter normalized by the sizing energy. Mask Error Factor (MEF) was defined as the ratio of critical dimension (CD) change for the resolved photoresist pattern to the relative dimension change on the mask pattern. Results from lithographic evaluation of formulations from Comparative Example 1 and Examples 1 are shown in Table 2.

TABLE 2

| Sample | Esize (mJ/cm²) | MEF | EL @ 10% of CD Target |
|---|---|---|---|
| Comparative | 16.6 | 4.06 | 10.1 |
| Invention PR1 | 30.3 | 3.3 | 11.9 |

As seen in Table 2, the photoresist formulation of the invention (PR1) prepared using the PAG from example 1 shows a higher exposure latitude and lower MEF values when compared with the nearly identical Comparative photoresist formulation but prepared using the commercially available triphenylsulfonium perfluorobutane sulfonate as the PAG.

Thus, PAGs from the present invention show the improved lithographic performance based on exposure latitude (EL) and mask error factor (MEF).

EXAMPLE 3

Synthesis of (4-((2,2-difluoro-3-(methacryloyloxy) propanoyl)oxy)phenyl)-diphenylsulfonium perfluorobutanesulfonate

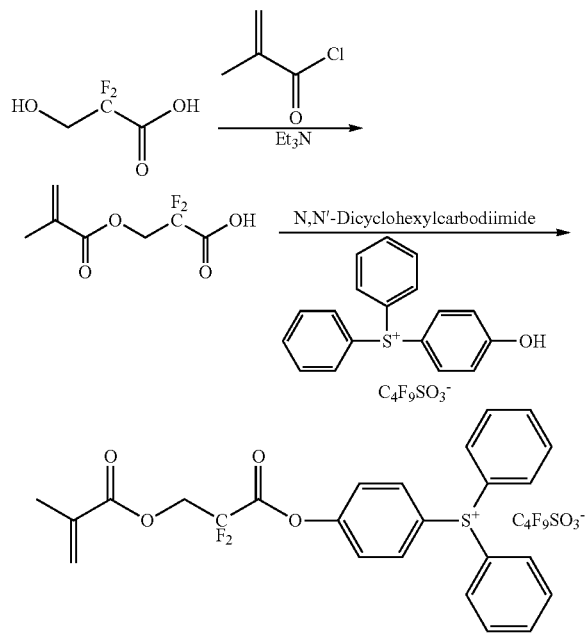

2,2-Difluoro-3-(methacryloyloxy)propanoic acid: To a mixture of 250 mL dichloromethane with 10.1 g (100 mmol) of triethylamine is added 12.6 g (100 mmol) of 2,2-difluoro-3-hydroxypropanoic acid and the resulting mixture is placed into an ice bath. 10.5 g (100 mmol) of methacryloyl chloride is added slowly into the flask and reaction is kept stirring for overnight. The resulting mixture is then washed with 200 mL of 1% NaHCO3 solution and the solvent is then subsequently removed. The product is then recrystallized from methanol to provide 2,2-difluoro-3-(methacryloyloxy)propanoic acid, in expected good yield, which is used for following synthesis without further purifications.

(4-((2,2-Difluoro-3-(methacryloyloxy)propanoyl)oxy) phenyl)diphenylsulfonium perfluorobutanesulfonate: To a mixture of 5 g (25.7 mmol) of 2,2-difluoro-3-(methacryloyloxy)propanoic acid in 100 mL of dichloromethane, 5.3 g (25.7 mmol) of N,N'-Dicyclohexylcarbodiimide and 0.06 g (0.5 mmol) of 4-Dimethylaminopyridine are added and stirred for 1 hour. 14.9 g (25.7 mmol) of p-hydroxyphenyl-dipheny perfluorobutanesulfonate is then added into the mixture and the mixture is stirred for 24 hours. After drying off the solvent, the resulting mixture is further purified by a silica gel column using a elution mixture of dichloromethane/methanol (90/10 v/v) 6.7 g (8.9 mmol) of pure (4-((2,2-difluoro-3-(methacryloyloxy)propanoyl)oxy)phenyl)diphenylsulfonium perfluorobutanesulfonate is obtained.

20.0 mmol of Vazo® 52 low-temperature polymerization initiator (E. I. du Pont de Nemours and Company) is added to a solution of 35.7 g (152.3 mmol) 2-methyl-2-adamantyl methacrylate, 25.9 g (152.3 mmol) 2-methyl-acrylic acid 2-oxo-tetrahydro-furan-3-yl ester, 17.4 g (76.2 mmol) hydroxynaphthylmethyl acrylate and 15.1 g (20.0 mmol) of the 4-((2,2-difluoro-3-(methacryloyloxy)propanoyl)oxy) phenyl)diphenylsulfonium perfluorobutanesulfonate in a 100 g acetonitrile:tetrahydrofuran 2:1 mixture. The monomers and initiator solution are degassed for 10 minutes. Under inert atmosphere, 5 mL of the monomer and initiator solution are introduced into a reactor which is preheated to 80° C. (oil bath). The remainder of the monomer and initiator mixture is fed into the reactor at 80° C. over a two hour period. Upon completion of the addition, the reaction mixture is refluxed for two additional hours. The mixture is next cooled to room temperature and the polymerization solution is precipitated into a large amount of diisopropyl ether, filtered and is then dried under vacuum. The resulting crude polymer is dissolved in 25-30 wt % tetrahydrofuran (THF) and precipitated into diisopropyl ether. The precipitated polymer is isolated by filtration and dried overnight at 40° C. under vacuum. The monomer structures for the polymeric bond PAG are summarized in following table.

| Monomers | Monomer 1 | Monomer 2 | Monomer 3 | Monomer 4 |
|---|---|---|---|---|
| Molar ratio(%) | 38 | 38 | 19 | 5 |
| Chemical Structures | | | | |

EXAMPLE 4

Polymers having monomers similar to those in Example 3 are prepared according to the general procedure of Example 3, except that each of the following PAG monomers (P1-P3) is used to prepare a PAG polymer.

(P1)
(P2)
(P3)

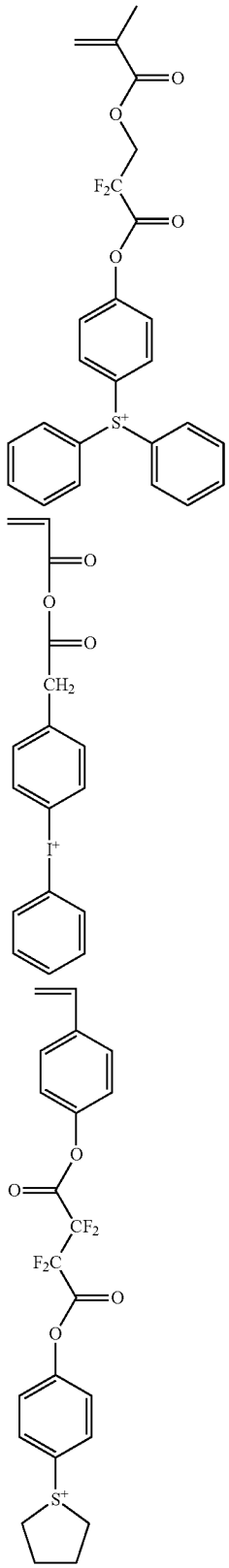

What is claimed is:

1. A photoacid generator compound of formula (I)

wherein each $R^1$ is chosen from $(C_1\text{-}C_{10})$alkyl, heteroatom-containing $(C_1\text{-}C_{10})$alkyl, fluoro$(C_1\text{-}C_{10})$alkyl, heteroatom-containing fluoro $(C_1\text{-}C_{10})$alkyl, $(C_6\text{-}C_{10})$aryl, and fluoro $(C_6\text{-}C_{10})$aryl; each $R^2$ is a chemical bond or a $(C_1\text{-}C_{30})$ hydrocarbyl group; each $R^3$ is H or a $(C_1\text{-}C_{30})$hydrocarbyl group; $R^5$, $R^6$ and $R^7$ independently are chosen from an optionally substituted carbocylic aryl group, an allyl group, and an optionally substituted $(C_1\text{-}C_{20})$alkyl group; X is a chemical bond or a divalent linking group; Z is chosen from an acetoacetoxy ester, —C(O)—O—C(O)—$R^1$—, —C(CF$_3$)$_2$—, —COO—$R^f$—, —SO$_3$—$R^f$—, —OCH$_{3-z}$(CH$_2$OC(=O)—$R^f$—)$_z$, and a $(C_5\text{-}C_{30})$cyclohydrocarbyl group comprising a base-reactive group chosen from fluoroalkyl esters, fluorosulfonate esters, and —C(CF$_3$)$_2$O—; each $R^f$ is independently a fluoro$(C_1\text{-}C_{10})$alkyl; p=0-6; w=1-3; x=1-4; y=0-5; z=1-2; r=0-1; M is S or I; wherein when M=I, r=0, and when M=S, r=1.

2. The photoacid generator compound of claim 1 wherein X is chosen from —C(O)O—, —C(O)S—, —SO$_3$—, —S(O)—, —SO$_2$—,

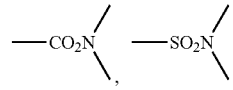

and combination thereof.

3. A photoresist composition comprising a photoacid generator compound of claim 1.

4. A method for forming a photoresist relief image on a substrate comprising: (a) applying a coating layer of a photoresist composition of claim 3 on a substrate; and (b) exposing the photoresist coating layer to patterned activating radiation and developing the exposed photoresist layer to provide a relief image.

5. The method of claim 4 further comprising developing the exposed photoresist layer with aqueous alkaline developer whereby the one or more base-reactive groups undergo a bond-breaking reaction to provide one or more polar groups.

6. The photoacid generator compound of claim 1 wherein $R^1$ is $(CR^a{}_2)_n$, wherein each $R^a$ is chosen from H, F, $(C_1\text{-}C_{10})$alkyl and fluoro$(C_1\text{-}C_{10})$alkyl; and n=0-6.

7. The photoacid generator compound of claim 1 wherein $R^3$ is chosen from H, $(C_1\text{-}C_{30})$alkyl, fluoro$(C_1\text{-}C_{30})$alkyl and $(C_6\text{-}C_{20})$aryl.

8. The photoacid generator compound of claim 1 wherein X is a divalent linking group of the formula —$X^2{}_{t1}$—$(Y^2=X^3)X^3{}_{t2}$—, wherein $X^2$=O, S, or NR; $Y^2$=C, S, or S=O, $X^3$=O or S; t1=0 or 1; and t2=0 or 1.

9. The photoacid generator compound of claim 1 wherein the photoacid generator of formula (I) has a structure

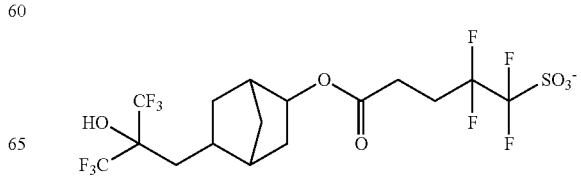

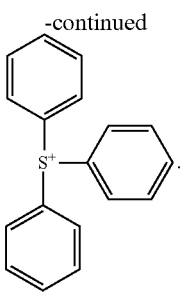
10. The photoacid generator compound of claim 1 wherein Z is —C(CF$_3$)$_2$O— or a (C$_5$-C$_{30}$)cyclohydrocarbyl group comprising —C(CF$_3$)$_2$O—; and R$^3$ is H.
* * * * *